United States Patent [19]

Brennan et al.

[11] 3,959,374

[45] May 25, 1976

[54] PROCESS FOR THE PREPARATION OF MIXED ISOMERIC METHYLENE-BRIDGED POLYCYCLOHEXYLPOLYAMINES

[75] Inventors: Michael E. Brennan; Ernest L. Yeakey, both of Austin, Tex.

[73] Assignee: Jefferson Chemical Company, Inc., Houston, Tex.

[22] Filed: May 30, 1974

[21] Appl. No.: 474,380

[52] U.S. Cl. .................................................. 260/563 B
[51] Int. Cl.² .................................................. C07C 87/40
[58] Field of Search .................... 260/563 D, 563 B

[56] References Cited
UNITED STATES PATENTS
3,376,341  4/1968  Bauer .......................... 260/563 D

*Primary Examiner*—D. Horwitz
*Attorney, Agent, or Firm*—James L. Bailey; Lee G. Meyer; John R. Kirk, Jr.

[57] ABSTRACT

A process is described for the preparation of mixed isomeric methylene-bridged polycyclohexylpolyamines wherein a mixed isomeric methylene-bridged polyphenyl polyamine mixture having a functionality of from about 2.0 to about 3.3 is pretreated by contacting the mixture and hydrogen with a nickel-containing hydrogenation catalyst at a temperature of from about 25°C. to about 250°C. under a pressure of about 500 to about 15,000 psig. The pretreated isomeric polyamine is then hydrogenated in the presence of ammonia under conventional hydrogenation conditions employing a ruthenium-containing hydrogenation catalyst. The pretreatment step allows the utilization of mixed isomeric methylene-bridged polyphenyl polyamine feed mixtures for the production of isomeric methylene-bridged polycyclohexylpolyamines in high yields without attendant deactivation of the ruthenium hydrogenation catalyst heretofore observed. The process is particularly applicable to continuous operation.

17 Claims, No Drawings

PROCESS FOR THE PREPARATION OF MIXED ISOMERIC METHYLENE-BRIDGED POLYCYCLOHEXYLPOLYAMINES

BACKGROUND OF THE INVENTION

1. Field of the Invention

This invention relates to processes for the hydrogenation of aromatic amines to corresponding alicyclic amines and more particularly pertains to the preparation of mixed isomeric methylene-bridged polycyclohexylpolyamines in high yields by the hydrogenation of mixed isomeric methylene-bridged polyphenyl polyamine feed mixtures. Isomeric methylene-bridged polycyclohexylpolyamines are useful in the preparation of polymeric materials such as polyamindes, polyisocyanates, and the like.

2. Description of the Prior Art

It is well-known that certain methylene-bridged polycyclohexylpolyamines, the dimers of which are sometimes referred to as di- or bis-(aminocyclohexyl)methanes, can be prepared by the hydrogenation of certain methylene-bridged polyphenyl polyamines utilizing certain noble metal catalysts. For example, U.S. Pat. No. 2,606,927 to Barkdoll, et al, 1952, describes a process wherein hydrogen is reacted with a dicarbocyclic diamine containing at least one benzene nucleus and having carbocyclic nuclei separated by at least one acyclic carbon atom, at a temperature of 225°–300°C. under a pressure of at least 500 atmospheres in the presence of ammonia and a nickel or cobalt hydrogenation catalyst. However, the described process has the distinct disadvantage of producing very low yields of desired products, e.g., below about 52.4%, and requires long reaction times approaching two to three hours. The overall combination of high temperature, high pressure and long reaction times also apparently increase the yield of undesirable solid by-products which are relatively useless.

Due to these disadvantages and others, the utilization of catalysts containing metallic ruthenium has become preferred in the art in such hydrogenation processes as described in U.S. Pat. Nos. 2,606,924; 2,606,925; 2,494,563; 3,347,917; 3,676,495; and others. U.S. Pat. No. 2,606,924 to Whitman (1952) and U.S. Pat. No. 2,494,563 to Kirk, et al. (1950) describe processes for the preparation of certain stereoisomeric bis (4-aminocyclohexyl)methanes by the hydrogenation of bis(4-aminophenyl)methane with a ruthenium metal catalyst in the presence or absence of volatile organic solvent. More particularly, Whitman (2,606,924) discloses that steroisomeric bis(4-aminocyclohexyl)methane mixtures liquid at normal temperatures can be produced by the hydrogenation of bis(4-aminophenyl)methane at a temperature of 75°–125°C. and a pressure of between 100–15,000 psi in the presence of a ruthenium catalyst. Kirk, et al. (2,494,563) teach that the hydrogenation of bis(4-aminophenyl)methane in the presence of a ruthenium catalyst at temperatures between 140°–250°C. and pressures above 500 psi, e.g., 1,500–3,500 psi, results in a reaction product which, upon distillation and redistillation in vacuo, provides stereoisomeric bis (4-aminocyclohexyl)methane mixtures having a freezing point above 40°C.

U.S. Pat. No. 2,606,925 to Whitman (1952) and U.S. Pat. No. 3,347,917 to Arthur (1967) both describe the preparation of steroisomeric di(para-aminocyclohexyl)methane rich in the trans,trans-stereoisomer by the hydrogenation of di(para-aminophenyl)methane in the presence of a ruthenium catalyst and ammonia. More particularly, Arthur (3,347,917) teaches that the desired product, liquid at room temperature, can be prepared in high yields above 90% in short reaction times by hydrogenating di(para-aminophenyl)methane at the temperatures of 180°–300°C. and pressures above 500 psi in the presence of 0.01% to 10% metallic ruthenium and 1% to 100% of ammonia, both based on the weight of the diamine feed. Patentee also discloses that the di(para-aminophenyl) methane feed prepared by conventional procedures, or obtained from commercial sources, can contain up to several percent impurities which are principally the ortho,para'-methylenedianiline. However, as more particularly discussed hereafter, it has been found that the presence of such isomeric impurities in the feed results in deactivation of the ruthenium catalyst and rapid decline in hydrogenation efficiency.

Further, U.S. Pat. No. 3,676,495 (1972) to Guenther describes the preparation of the triamine 2,4-bis(aminocyclohexylmethyl)cyclohexylamine by hydrogenation of 2,4-bis(p-aminobenzyl)aniline in the presence of a ruthenium metal catalyst and ammonia as described in U.S. Pat. No. 2,606,925, supra.

As evidenced by the above references, hydrogenation of methylene-bridged polyphenyl polyamines in the presence of ruthenium catalysts normally includes employment of substantially pure feeds, e.g., 4,4'-methylenedianiline, substantially free from other isomers such as 2,4'- and 2,2'-methylenedianiline isomers. These feeds are prepared by the well-known condensation reaction of aniline and formaldehyde in the presence of a strong mineral catalyst, such as HCl, or a silica-alumina catalyst. The well-known condensation reaction generally produces a mixed isomereic condensation product containing methylenedianiline isomers and higher functionality polyphenyl polyamines and their isomers. As known, the amounts of particular isomers and higher functionality polyphenyl polyamines can be controlled to some extent by control of condensation reaction process conditions. Yet, substantially pure feeds have heretofore usually been obtained by further isolating a particularly desired isomer from the condensation reaction product such as by fractional distillation.

From an economic standpoint, it would be desirable to prepare methylene-bridged polycyclohexylpolyamine products by the hydrogenation of the mixed isomeric condensation reaction products without the requirement of isolating substantially pure feeds. It is well-known that mixed isomeric methylene-bridged polyphenyl polyamines can be hydrogenated to the corresponding mixed isomeric methylene-bridged polycyclohexylpolyamines by the employment of ruthenium-containing hydrogenation catalysts. However, such hydrogenation of methylene-bridged polyphenyl polyamines suffers from the disadvanatage of rapidly deactivating ruthenium-containing hydrogenation catalysts. Apparently, these mixed isomeric polyamines "poison" ruthenium catalysts. In continuous hydrogenation systems, the rapid deactivation of the ruthenium catalyst results in partial and eventual cessation of hydrogenation, which further results in low yields of hydrogenated product.

Such catalyst deactivation requires that the catalyst be frequently replaced with fresh active catalyst. Moreover, such deactivation can result in partial loss of the ruthenium metal or catalyst activity. Ruthenium-containing hydrogenation catalysts are very expensive and, therefore, in view of these disadvantages, it has heretofore been more economical to employ substantially pure polyamine feeds in hydrogenation processes utilizing ruthenium catalysts.

We have now discovered a process for hydrogenating mixed isomeric polyphenyl polyamine mixtures employing a ruthenium-containing hydrogenation catalyst that does not result in catalyst deactivation or otherwise adversely affect the catalyst activity. In our process, mixed isomeric polyphenyl polyamine feed mixtures are pretreated by initially contacting the feed mixtures with a nickel-containing hydrogenation catalyst. Surprisingly, the pretreatment in accordance with the present invention apparently removes catalyst poisons in the feed or otherwise prevents ruthenium catalyst deactivation and results in the production of mixed isomeric methylene-bridged polycyclohexylpolyamines in very high yields, e.g., above 90% based on the weight of the polyamine feeds.

SUMMARY OF THE INVENTION

This invention provides a process for the preparation of mixed isomeric methylene-bridged polycyclohexylpolyamines in high yields from mixed isomeric methylene-bridged polyphenyl polyamine mixtures comprising the steps of pretreating the polyamine mixtures by contacting, in the presence of hydrogen, the isomeric methylene-bridged polyphenyl polyamine mixture with a nickel-containing hydrogenation catalyst at a temperature of between about 25° to about 250°C. under a pressure of about 500 to about 15,000 psig, and then hydrogenating the pretreated isomeric feed mixture by heating it with the hydrogen at a temperature of about 150° to about 250°C. under a pressure of about 500 to about 15,000 psig in the presence of ammonia and a ruthenium-containing hydrogenation catalyst. The process is particularly adaptable to continuous operation whereby flowing streams of hydrogen, and the mixed isomeric methylene-bridged polyphenyl polyamine mixture are injected into a first pretreatment zone, having a temperature between about 25°C. to about 250°C. and a pressure of about 500 to about 15,000 psig and which contains the nickel hydrogenation catalyst. The flowing streams of hydrogen and isomeric polyamine feed are passed through the first zone at a space velocity of between about 0.5 to about 2.5 grams total liquid per ml. catalyst per hour whereby the streams come into intimate contact with the nickel catalyst. The flowing streams, along with a flowing stream of ammonia, are then passed through a second reaction zone having a temperature within the range of about 150°C. to about 250°C., a pressure of between about 500 to about 15,000 psig and containing the ruthenium hydrogenation catalyst. The flow streams are passed through the second zone, and thus come in intimate contact with the ruthenium catalyst to provide hydrogenation of the polyphenyl polyamine mixture. The resulting isomeric methylene-bridged polycyclohexylpolyamines can then be recovered from the hydrogenated reactant stream by known product separation techniques. The inventive process may be carried out in the presence or absence of a liquid organic solvent which is not susceptible to hydrogenation conditions. As more particularly described hereafter, the pretreatment steps can be carried out in the presence or absence of ammonia. However, in order to produce high yields of desired hydrogenated products, it is essential that ammonia be present during the hydrogenation in the presence of the ruthenium catalyst.

DETAILED DESCRIPTION OF THE INVENTION

As briefly described hereinbefore, mixed isomeric methylene-bridged polyphenyl polyamine mixtures are prepared by the well-known condensation reaction of formaldehyde and aniline in the presence of a strong mineral acid such as hydrochloric acid or catalysts such as silica-alumina catalysts. The condensation reaction products generally contain mixtures of isomeric diamines, e.g., 2,2'-, 2,4'- and 4,4'-methylenedianilines and higher functionality isomeric polyamines, e.g., triamines, tetramines, and the like. As know, the particular amount of diamine, higher functionality polyamines and the isomeric ratios thereof for a given condensation reaction product mixture can be varied greatly, such as by altering reactant ratios, catalysts and reaction conditions, as well as employing particular product purification and/or separation techniques. These various procedures and techniques are well-known in the art and need not be discussed herein. Usually these methylene-bridged polyphenyl polyamine condensation reaction products are described as having an average functionality, from about 2.0 for substantially pure methylenedianiline product to higher functionality, depending upon the presence of higher functionality polyamines. Techniques for determining the average functionality of a given mixture are also well-known in the art and will not be further described herein.

The present invention is adaptable for the preparation of isomeric methylene-bridged polycyclohexylpolyamines from any methylene-bridged polyphenyl polyamine isomeric mixture which can be prepared by any known condensation reaction process. However, we prefer to employ such feed mixtures that have average functionalities of 2.0 to about 3.3, preferably from about 2.0 to about 2.7.

The feed mixtrue employed preferably contains at least about 25.0% isomeric methylenedianilines, based upon the weight of the total feed mixture, but such amount is not critical to the invention. Further, preferred feed mixtures contain methylenedianiline isomeric ratios of between about 1% to 10% 2,2'-:10% to 70% 2,4'-:20% to 90% 4,4'-isomers, based upon the weight of the methylenedianiline present. It will be understood, however, that substantially pure methylene-bridged polyphenyl polyamine feeds, e.g., bis(4-aminophenyl) methane, may be used if desired.

An example of a particularly useful methylene-bridged polyphenyl polyamine isomeric mixture is one having an average functionality of about 2.0 which contains about 96.1 wt.% methylenedianiline, 3.7 wt.% higher functionality polyamines and the remainder impurities, which has a methylenedianiline isomeric ratio of about 4.4:23.9:71.6 for the 2,2'-:2,4'-:4,4'-isomers shown as area percents on the gas chromatogram. Examples of other particularly useful isomeric polyphenyl polyamine mixtures are those having an average functionality between about 2.2 to about 2.7 prepared by the process described in U.S. Pat. No. 3,362,979, issued to Bentley on Jan. 9, 1968, which is incorporated herein by reference.

In accordance with the present invention, the mixed isomeric methylene-bridged polyphenyl polyamine mixture is initially contacted, in the presence of hydrogen, with a nickel-containing hydrogenation catalyst at a temperature within the range of from about 25°C. to about 250°C. under a pressure of about 500 to about 15,000 psig in any manner known in the art. For example, the isomeric polyamine mixture and hydrogen can be passed over and/or through a stationary bed of catalyst, as more particularly discussed hereafter, or admixed with the catalyst in a suitable pressure reactor vessel. Preferably, the isomeric polyamine feed and hydrogen are intimately contacted with the nickel catalyst at a temperature between about 150° to about 210°C. Although higher pressures than hereinbefore described can be utilized, such are usually uneconomical and such higher pressures do not appear to affect the process. We prefer to employ pressures sufficient to maintain the pretreatment medium liquids in liquid phase, e.g., within the range of about 1,500 to about 3,500 psig.

Any conventional hydrogenation catalyst containing nickel as the active catalytic component can be employed in the pretreatment step of the present invention. Types of nickel hydrogenation catalysts are well-known in the art and include those wherein the active catalytic component contains elemental nickel, raney nickel, nickel oxides, nickel salts, and the like. These nickel hydrogenation catalysts can be used as non-supported or supported on a carrier inert to process conditions such as refractory support, charcoal, silica, alumina, and the like. Such supported catalysts and methods for their preparation are well-known in the art. Moreover, the catalysts can be employed in any conventional manner, such as in highly divided form or pelleted form and as a slurry or stationary bed. We prefer to utilize a pelleted supported nickel hydrogenation catalyst containing about 30% to 55% elemental nickel based upon the weight of metal present in a stationary bed. An example of a useful nickel catalyst includes Girdler T-1647C-RS, Chemtron Corporation, Chicago, Ill., which is a supported pelleted catalyst containing 53.5% elemental nickel on a refractory support.

Preferably, at least a 100% molar excess of hydrogen, based upon the polyamine mixture, is utilized in the pretreatment step. However, the particular amount of hydrogen utilized has not been found to be critical. The hydrogen can be admixed with the isomeric polyamine feed mixture prior to or during the contacting of the mixture with the nickel-containing hydrogenation catalyst and can be utilized in admixture with an inert gas, such as nitrogen.

The pretreatment of the mixed isomeric polyamine feed mixture can be carried out in the presence or absence of ammonia. Experiments have shown that such presence or absence of ammonia does not adversely affect the results obtained. However, as illustrated in one of the examples set forth hereafter, subsequent hydrogenation of the mixed isomeric polyamine feed in the presence of the ruthenium-containing hydrogenation catalyst must be carried out in the presence of ammonia in order to obtain high yields of the desired product. The presence of ammonia during hydrogenation reduces the tendency of the formation of higher molecular weight polyamines. Thus, ammonia can be added during the subsequent hydrogenation step discussed hereafter. However, for convenience, we prefer to carry out the aforementioned pretreatment step in the presence of ammonia. The ammonia can be added prior to or during the contacting of the mixed isomeric polyamine feed mixture and hydrogen with the nickel catalyst. Preferably, anhydrous ammonia is employed in molar ratios of ammonia:isomeric polyamine feed mixture of betwen about 3:1 to about 30:1, with molar ratios of between about 6:1 to about 10:1 being optimal. Greater amounts of ammonia can be utilized if desired without any harmful effect on yields, but economic considerations would then control the amount.

The pretreatment step can also be carried out in the presence or absence of an organic liquid solvent which includes the saturated alicyclic and aliphatic hydrocarbons, hydrocarbon ethers, hydrocarbon alcohols, alkylamines and the like. Examples of such solvents include dioxane, n-heptane, cyclohexane, butyl ethers, isopropyl alcohol, and butyl alcohols, to name just a few. We prefer to utilize hydrocarbon alcohols such as isopropyl alcohol or t-butyl alcohol. As known, certain hydrocarbon alcohols, e.g., isopropyl alcohol, can undergo at least a partial amination under hydrogenation conditions. Nevertheless, these side reactions are substantially insignificant in regard to the inventive process and do not affect the utilization of such alcohols as a solvent. Mixtures of solvents can also be employed, if desirable. The solvent can be utilized in any desired amount, but we prefer to utilize a concentration of between about 70 to about 90%, based upon the weight of the mixed isomeric polyamine-solvent mixture.

The length of pretreatment time in the process of the invention has not been found to be critical. The only critical factor is to obtain intimate contact of the mixed isomeric polyamine mixture with the nickel-containing hydrogenation catalyst. For convenience, in batch processing under the aforementioned preferred conditions, we prefer to carry out the pretreatment in about 15 minutes to about 1 hour. In continuous processing, under the aforesaid preferred conditions, we prefer to carry out the pretreatment step at a space velocity of from about 0.5 to about 2.0 g. total liquid feed/ml. of catalyst/hour. As known, space velocity is a conventional way of measuring rates in continuous processing. The skilled artisan can readily determine the amount of time to employ for intimate contact of a particular isomeric polyamine feed with the nickel-containing hydrogenation catalyst under particular processing conditions for a reading of this specification and examples without undue experimentation inasmuch as said contact time is not critical.

As previously mentioned, the pretreatment step of contacting the mixed isomeric polyamine mixture with the nickel catalyst apparently removes or inactivates poisons from the mixed isomeric methylene-bridged polyphenyl polyamine feed mixtures that heretofore have rapidly deactivated hydrogenation catalysts containing ruthenium as the active catalytic component. Surprisingly, however, it has been found that practically no other change occurs to the feed mixture in the pretreatment step. For example, analysis of the pretreated polyamine effluent shows that substantially no hydrogenation occurs.

In accordance with the present invention, the pretreated feed mixture can then be hydrogenated by heating the isomeric mixture, hydrogen and ammonia in the presence of a ruthenium-containing hydrogenation catalyst to a temperature within the range of about 150° to about 250°C., preferably about 180° to 210°C., under a pressure of between about 500–15,000 psig sufficient to maintain the liquids present in the liquid phase, preferably about 1,500 to about 3,500 psig. Ruthenium-type hydrogenation catalysts are well-known as are the above-described nickel metal hydrogenation catalysts, and any of these well-known types can be employed in the practice of the invention. Well-known types of conventional ruthenium catalysts are described in U.S. Pat. No. 3,347,917, issued to Arthur on Oct. 17, 1967, which is hereby incorporated by reference. We prefer to utilize a catalyst containing about 0.01% to about 10% ruthenium metal on a carrier that is inert under the hydrogenation conditions, such as carbonates and the like. Such supported ruthenium catalysts and the processes for their manufacture are well-known in the art, as disclosed in U.S. Pat. No. 3,347,917. Moreover, the catalyst can be utilized in slurry form or as a stationary bed. We prefer to employ a stationary bed of pelleted catalyst containing about 0.5% by weight ruthenium metal supported on a carbonate carrier.

The pretreated effluent is heated in the presence of the ruthenium metal catalyst for a time period sufficient to provide substantially 100% hydrogenation of the isomeric polyamine. Analyses of the hydrogenated effluent have shown that particular hydrogenation times are not critical. Usually in batch processing under the preferred hydrogenation conditions set forth hereinabove, substantially 100% hydrogenation occurs in about 15 minutes to about 120 minutes. In continuous processing, we prefer to employ space velocities within the range of from about 0.5 to about 2.0 g. total liquid per ml. catalyst per hour.

The hydrogenated effluent can then be processed by any of the well-known separation methods to obtain the desired mixed isomeric methylene-bridged polycyclohexylpolyamine product, such as by fractional distillation and the like. If desired, the hydrogenated isomeric dimers can be further separated from each other and/or the higher functionality methylene-bridged polycyclohexylpolyamines by such conventional fractional distillation techniques. Analyses of the process effluents show that essentially 100% conversion of the mixed isomeric methylenedianilines and higher functionality polyphenyl polyamines are obtained which results in correspondingly high yields of the desired mixed methylene-bridged polycyclohexylpolyamine products. Such results are obtained without deactivation or reduction in the hydrogenation efficiency of the ruthenium catalyst which allows reuse of the catalyst without reactivation or the continuous use of fresh catalyst.

For these reasons, the present invention is especially adaptable for continuous processing, utilizing any well-known continuous processing systems and equipment. For instance, in a preferred embodiment of the invention, mixed isomeric methylene-bridged polycyclohexylpolyamines can be continuously produced by injecting continuous flowing streams of the mixed isomeric methylene-bridged polyphenyl polyamine feed mixture, hydrogen and ammonia into a first pretreatment zone which has a temperature of between about 150°C. to about 210°C. and a pressure between about 1,500 to about 3,500 psig and contains the nickel-containing hydrogenation catalyst such as described hereinbefore. Any conventional chemical processing apparatus known in the art capable of maintaining the described temperatures and pressures can be utilized as the first pretreatment zone. For example, we prefer to utilize conventional continuous pressure reactors. The nickel-containing hydrogenation catalyst is maintained in the first zone in any conventional manner, such as by support on a stationary bed, which eliminates subsequent catalyst removal from the flowing streams of reactants.

The flowing streams of the above-described reactants may be admixed prior to injection or injected substantially simultaneously into the first pretreatment zone. Preferably, the mixed isomeric polyamine stream includes the polyamine mixture diluted in an organic solvent in an amount to provide about 70% to about 90% solvent, based on the weight of the polyamine-solvent stream. The flowing streams are injected at respective rates sufficient to provide at least 100% molar excess hydrogen, based on the mixed isomeric polyamine feed, and a molar ratio of from about 6 to about 10 moles ammonia per mole of isomeric polyamine feed. The hydrogen stream preferably contains an admixture of hydrogen and an inert gas such as nitrogen. Moreover, the ammonia is preferably injected in its anhydrous form. However, as mentioned hereinbefore, it is not essential to inject a stream of ammonia with the first zone containing the nickel catalyst. Such is preferred, for convenience.

The flowing reactant streams are passed through the first pretreatment zone at respective rates sufficient to provide a space velocity through the zone of between about 0.5 to 2.0, and preferably 1.0, g. total liquid/ml. catalyst/hour, whereby intimate contact of the polyamine feed and catalyst is obtained. As previously mentioned, such treatment of the flowing streams under such conditions has been found to produce substantially no chemical reactions which can be analyzed. Analysis of the flowing streams show substantially the same materials in substantially the same proportions as initially injected into the first zone.

The flowing reactant streams are then passed at a space velocity of between about 0.5 to about 2.0, preferably 1.0, g. total liquid/ml. catalyst/hour through a second reaction zone which has a temperature within the range of from about 150°C. to about 250°C. and a pressure of between about 500 to about 15,000 psig, and contains a ruthenium metal hydrogenation catalyst therein. Preferably, the second reaction zone is maintained at about 180° to about 210°C. with a pressure within the range of between about 1,500 to about 3,500 psig. The flowing streams are passed through the second reaction zone at a space velocity sufficient to allow substantially complete hydrogenation of the polyamine feed mixture. The second reaction zone can also be any conventional apparatus capable of maintaining the described temperatures and pressures with the described reactants present therein, such as a conventional continuous pressure reactor. The ruthenium-containing hydrogenation catalyst is preferably supported within the second zone on a stationary bed for the reasons mentioned hereinbefore.

The desired mixed isomeric methylene-bridged polycyclohexylpolyamines can then be recovered from the flowing reactant stream by subjecting hydrogenated effluent to conventional separation procedures, such as by distillation.

Experiments have shown that such a continuous process as described hereinabove can be run for extended periods of time to provide high yields of the desired hydrogenated product with substantially no ruthenium catalyst deactivation. Any desired mixture of isomeric methylene-bridged polyphenyl polyamine mixtures can be employed which provides economic advantages over conventional processes which require the use of substantially pure polyamine feeds.

The following examples are for purposes of illustration of our invention and are not to be limiting thereof. Parts and percentages are by weight, unless otherwise indicated.

EXAMPLE I

In this experiment, two consecutive 500 ml. continuous vertical tubular reactors (each 316 stainless steel, 1¼ inch ID × 29-9/16 inch long) were connected in series by appropriate conduits for continuous processing runs. The first reactor contained a stationary bed of 475 ml. ⅛-inch extrusions of Girdler T-1647C-RS nickel catalyst (Chemtron Corporation, supra). This catalyst contained about 53.5% nickel metal on a refractory support. The first reactor was equipped with inlet systems for continuous introduction of anhydrous ammonia, hydrogen and a solvent: isomeric methylene-bridged polyphenyl polyamine feed mixture, and an outlet system for continuous removal of the pretreated effluent. The second reactor contained a stationary bed of 475 ml. 1/16-inch extrusions of a ruthenium catalyst which contained 0.5 wt.% ruthenium metal on a carbonate support. The second reactor also was equipped with inlet and outlet systems for continuous introduction and removal of effluent. The reactors were electrically heated with temperature being sensed by thermocouples at several points within the reactors. The temperature of each reactor was controlled by an automatic preset temperature controller. The first reactor was heated to about 150°C. while the second reactor was heated to between about 185°–200°C. Isopropyl alchohol, preheated to about 50° to about 60°C., was pumped through steam traced feed lines into the reactor system which was continuously flushed therewith for two hours at or near the aforesaid temperatures for each reactor while each reactor was pressurized to about 2625–2725 psig. A feed mixture of 30 wt.% isomeric methylenedianiline, 96.1 wt.% methylenedianiline (MDA), 3.7 wt.% poly-MDA by GLC; MDA area percent ratio of 4.4:23.9:71.6 for 2,2'–:2,4'–:4,4'-isomers by GLC (Jefferson Chemical Company, Inc., Houston, Texas) and 70 wt.% isopropyl alcohol, preheated to about 50°C. to about 60°C. was then pumped through the steam traced feed lines as one stream into the first reactor at a rate of 1.0 lb./hr. Anhydrous ammonia was simultaneously pumped as a second stream into the reactor at 0.2 lbs./hr. while 385 l./hr. (STP) 75:25 volume % hydrogen:nitrogen was metered therein through a calibrated rotometer as a third stream. The three streams were passed through the first reactor and fed directly through the second reactor. The three streams passed through each reactor at a space velocity of abot 1.0–1.25 g. total liquid feed/ml. catalyst/hour with a design of a space velocity of 1.15 and a mole ratio of ammonia to polyamine feed of 8.0 to 1.0. After a short pre-run, the continuous reaction was carried out for 5½, 7½, and 7.0 hours of on stream time over a three-day period (total 19 7/12 hours). Six samples of the effluent from the first reactor were taken from the conduit between the first and second reactors and analyzed. Analysis of the samples showed that less than 1% hydrogenation had occurred in the first reactor and that no other significant chemical reactions had taken place. The effluent from the second reactor was a colorless liquid which by GLC was shown to contain (average) 0.7% methylenedianiline (2,4'-and 4,4'–), 0.2% aminobenzylcyclohexylamine (one-half hydrogenated product), 89.2% methylene di-cyclohexylamine, 6.4% cyclohexylmethylcyclohexylamine (a hydrogenolysis product; acridane derived from 2,2'-MDA may also be present), and 3.5% unknown (possible MDCHA isomer). The NMR spectrum analysis of the concentrated effluent showed no aromatic protons and was consistent for methylene di-cyclohexylamine.

The continuous process was continued on stream under the same reaction conditions on the same catalysts for a total of 205¾ hours. Samples of the hydrogenation reaction effluent were taken at designated times and analyzed. The analytical results are set forth in the following Table 1.

Table 1

| Reactor No.2, Temp., °C. | Hours | Total Hours | Avg. GLC Area % Reactor No. 2 Effluent | | | | |
|---|---|---|---|---|---|---|---|
| | | | CMCHA[1] | MDCHA[2] | Unknown[3] | ABCHA[4] | MDA[5] |
| 200 | 20-1/4 | 39-10/12 | 6.2 | 90.7 | 2.9 | 0.2 | 0.0 |
| 195 | 19 | 58-10/12 | 5.6 | 92.9 | 1.1 | 0.3 | 0.0 |
| 195 | 21-3/4 | 80-3/12 | 6.2 | 91.1 | 1.5 | 1.0 | 0.1 |
| 190 | 19-1/12 | 99-2/3 | 5.6 | 91.3 | 1.2 | 1.9 | 0.0 |
| 185 | 22 | 121-2/3 | 5.4 | 90.6 | 1.0 | 2.6 | 0.3 |
| 190 | 22-7/12 | 144-1/4 | 5.7 | 91.8 | 1.2 | 0.9 | 0.4 |
| 195 | 22-3/4 | 167 | 6.0 | 92.4 | 1.1 | 0.6 | 0.0 |
| 200 | 20-3/4 | 187-3/4 | 6.6 | 90.5 | 1.8 | 1.0 | 0.0 |
| 200 | 18 | 205-3/4 | 5.8 | 88.0 | 1.0 | 5.0 | 0.0 |

[1]CMCHA = cyclohexylmethylcyclohexylamine (a hydrogenolysis product; acridane derived from 2,2'-MDA may also be present)
[2]MDCHA = methylene di-cyclohexylamine
[3]Unknown = possible MDCHA isomer
[4]ABCHA = aminobenzylcyclohexylamine (one-half hydrogenated product
[5]MDA = methylenedianiline As Table 1 illustrates, substantially 100% conversion of MDA is obtained with approximately 90% yield of methylene di-cyclohexylamine. Moreover, the data in the Table illustrates that the yield of MDCHA is maintained substantially over the entire on stream time, proving the continued activity of the ruthenium catalyst.

EXAMPLE II

In this experiment, the second reactor described in Example I was equipped with suitable inlet systems for continuous introduction of liquids and hydrogen, charged with 475 ml. fresh 0.5% ruthenium on carbonate catalyst, heated to about 200°C. and pressurized to between about 2625–2725 psig while being flushed with isopropyl alcohol preheated to 50°–60°C. After the flushing, a feed mixture of 30:70 wt.% pure 4,4'- methylenedianiline:isopropyl alcohol, heated to 60°C., was continuously introduced as one stream into the reactor at 1.0 lbs./hr. Simultaneously, 0.2 lbs./hr. anhydrous ammonia and 385 l./hr. (STP) 75:25 (volume %) hydrogen:nitrogen were continuously introduced into the reactor. The feed rates of the stream of materials provided a space velocity of 1.0–1.25 through the reactor. On stream time was continued for 100-11/12 hours total time with an attempt to maintain the reaction conditions substantially the same as set forth in Example I. Samples of the reaction product effluent were taken at designated times and analyzed. The results are set forth in the following Table 2.

during the on stream time are set forth in the following Table 3.

Table 3

| Temp., °C. | Hours | Total Hours | GLC Area %, Effluent | | | |
|---|---|---|---|---|---|---|
| | | | CMCHA | MDCHA | ABCHA | MDA |
| 200 | 7 | 7 | 3.2 | 75.1 | 19.9 | 1.2 |
| 201 | 7 | 14 | 3.1 | 72.1 | 23.5 | 0.9 |
| 202 | 7 | 21 | 3.0 | 69.2 | 26.8 | 0.5 |
| 198 | 7 | 28 | 2.1 | 58.1 | 37.0 | 2.4 |
| 197 | 6-3/4 | 34-3/4 | 1.4 | 45.5 | 46.2 | 6.6 |
| 197 | 5-3/4 | 40-1/2 | 1.7 | 48.1 | 44.8 | 5.1 |
| 210 | 5-1/4 | 45-3/4* | 2.3 | 58.5 | 36.8 | 1.9 |
| 209 | 15-1/4 | 61 | 1.5 | 40.6 | 48.5 | 9.0 |
| 225 | 4 | 65 | 1.5 | 49.2 | 44.5 | 4.2 |
| 221 | 16 | 81 | 1.3 | 45.6 | 45.9 | 6.5 |

*Isopropyl alcohol wash, two hours.

As shown in Table 3, the yields of MDCHA and conversions of MDA progressively fell during continuous hydrogenation over the same ruthenium catalyst. The data of Table 3 illustrates that the ruthenium catalyst was progressively partially deactivated. Moreover, solvent washing of the catalyst and higher temperatures did not significantly increase the catalyst activity, particularly for any length of time.

EXAMPLE IV

The continuous dual reactor system described in

Table 2

| Temp., °C. | Hours | Total Hours | Avg. GLC Area %, Effluent | | | |
|---|---|---|---|---|---|---|
| | | | CMCHA | MDCHA | ABCHA | 4,4'-MDA |
| 199 | 17-5/6 | 17-5/6 | 2.8 | 93.3 | 3.7 | 0.0 |
| 195 | 36-2/3 | 36-2/3 | 2.4 | 94.6 | 2.9 | 0.0 |
| 200 | 7 | 43-1/3 | 2.3 | 90.6 | 6.7 | 0.0 |
| 202 | 15-3/4* | 59-5/12 | 1.1 | 76.4 | 21.0 | 0.0 |
| 201 | 19 | 78-5/12 | 2.1 | 92.3 | 2.9 | 0.0 |
| 194 | 5-1/2 | 83-11/12 | 1.9 | 91.4 | 4.7 | 0.0 |
| 193 | 17** | 100-11/12 | 1.5 | 86.7 | 10.7 | 0.0 |

*During the run, ammonia pump failed and only about one-third of the described ammonia poundage was injected.
**During run, hydrogen:nitrogen injection rate fell below described rate.

The results of Table 2 show that the hydrogenation of pure 4,4'-methylenedianiline over a ruthenium catalyst proceeds smoothly without catalyst deactivation. Thus, a pretreatment step is not required for successful hydrogenation of this pure feed. Table 2 also illustrates the requirement of conducting the hydrogenation in the presence of ammonia, as shown by the lower yield of MDCHA when the amount of ammonia present was about one-third the described poundage.

EXAMPLE III

Experiment II was repeated utilizing the same second reactor and ruthenium catalyst and process conditions except that the 4,4'-methylenedianiline:solvent feed was replaced by the mixed isomeric methylenedianiline:solvent feed mixture described in Example I as the one feed stream. The hydrogenation was continued for a total on stream time of 81 hours with samples being taken intermittently. After an on stream time of 40½ hours, the feed was switched to isopropyl alcohol and the catalyst washed for two hours while the temperature of the reactor was maintained at about 195°–213°C. After 61 hours of on stream time, the temperature was increased and maintained for about 4 hours at about 225°C., and then reduced and maintained at about 221°C. for the remaining 16 hours of on stream time. Analytical results of the samples taken Example I was employed in this experiment. Both reactors were pressurized to between about 2660–2700 psig and heated to 150° and 200°C., respectively, while the entire system was flushed with isopropyl alcohol for 2.0 hours preheated to 50°–60°C. The feed was then switched to simultaneous continuous injection of 385 l./hr. (STP) 75:25 (volume %) hydrogen:nitrogen, 0.2 lbs./hr. anhydrous ammonia, and 1.0 lbs./hr. feed of 80 wt.% isopropyl alcohol:20 wt.% of a mixed isomeric methylene-bridged polyphenyl polyamine mixture having an average functionality of about 2.2 containing 65.9 wt.% isomeric MDA, 34.1 wt.% higher molecular weight and higher functionality isomeric poly-MDA, and having a MDA area percent ratio of 3.2:22.4:74.4 for 2,2'–:2,4'–:4,4'-MDA isomers by GLC (JEFFAMINE AP-22, Jefferson Chemical Company, Inc., Houston, Texas). The polyamine:solvent feed stream was preheated to 50°–60°C. prior to injection. Continuous reaction was carried out for a total on stream time of 41 hours. During the on stream time, the pressure in both reactors varied between 2660–2700 psig and the temperature in the second reactor was varied between 200°–225°C. Also, the amine/isopropyl alcohol and ammonia feed rates varied between about 0.45–1.35 lbs./hr. and 0.20–0.30 lbs./hr., respectively, to provide space velocities of between about 0.65–1.58 g. total liquid/ml. catalyst/hr. The average of analytical results of samples taken intermittently during the on stream time gave 97.9–99.8% total aromatic amine conversion. The fate of the isomeric poly-MDA was determined from the ratio of aliphatic to aromatic protons in the crude product effluent by NMR analysis.

EXAMPLE V

The process of Example IV was repeated employing the same continuous dual reactor system, process conditions and feed rates of ammonia, hydrogen:nitrogen, and solvent: isomeric polyamine (1.0 lbs./hr.), except that the solvent: polyamine feed stream was comprised of 90 wt.% isopropyl alcohol and 10 wt.% of a mixed isomeric methylene-bridged polyphenyl polyamine mixture having an average functionality of about 2.7, containing 49.9 wt.% isomeric MDA, 50.1 wt.% higher molecular weight and higher functionality isomeric poly-MDA and having an MDA area percent ratio of 3.6:21.2:75.2 for 2,2'-:2,4'-:4,4'-MDA isomers by GLC (JEFFAMINE AP-27, Jefferson Chemical Company, Inc., Houston, Texas). During continuous processing, the solvlent/polyamine and ammonia feed rates varied, as in Examples IV, to provide space velocities of between about 0.72–1.52 g. total liquid/ml. catalyst/hr. Continuous processing was maintained for a total on stream time of 40 hours, with intermittent sampling of the hydrogenated product effluent which, upon analysis, gave an average of 92.6–100.0% aromatic amine conversion.

EXAMPLE VI

The experiment described in Example IV was repeated except that t-butyl alcohol was used as the solvent in the place of isopropyl alcohol. The space velocity varied between 0.68–1.15. Analysis of samples taken during the on stream time of 41 hours showed 99.1–100.0% aromatic amine conversion.

Many modifications and variations of the invention as hereinbefore set forth may be made without departing from the spirit and scope thereof.

We claim:

1. In a process for the preparation of mixed isomeric methylene-bridged polycyclohexylpolyamines comprising hydrogenating a mixed isomeric methylene-bridged polyphenyl polyamine mixture at a temperature within the range of about 150° to about 250°C under a pressure of about 500 to about 15,000 psig in the presence of ammonia and a ruthenium-containing hydrogenation catalyst, the improvement comprising:
    initially intimately contacting, in the presence of hydrogen, the mixed isomeric methylene-bridged polyphenyl polyamine mixture with a nickel-containing hydrogenation catalyst at a temperature of between about 25° to about 250°C under a pressure of about 500 to about 15,000 psig and for a time effective in preventing the rapid deactivation of said ruthenium-containing hydrogenation catalyst in said hydrogenating step; and then
    hydrogenating said mixed isomeric methylene-bridged polyphenyl polyamine mixture in the presence of said ammonia and said ruthenium-containing hydrogenation catalyst.

2. A process in accordance with claim 1 wherein said mixed isomeric methylene-bridged polyphenyl polyamine mixture is comprised of isomeric 2,2'-, 2,4'- and 4,4'- methylenedianiline and higher functionality polyphenyl polyamines, said mixture having an average functionality of from about 2.0 to about 3.3.

3. A process in accordance with claim 1 wherein said mixed isomeric methylene-bridged polyphenyl polyamine mixture contains at least about 25 wt.% mixed isomeric methylenedianiline.

4. A process in accordance with claim 1 wherein said mixed isomeric methylene-bridged polyphenyl polyamine mixture contains isomeric methylenedianiline in ratios of between about 1% to 10% 2,2'-:10% to 70% 2,4'-:20% to 90% 4,4'-methylenedianiline isomers based upon the weight of said isomeric methylenedianiline.

5. A process in accordance with claim 1 wherein said mixed isomeric methylene-bridged polyphenyl polyamine mixture has a functionality of between about 2.2 to about 2.7.

6. A process in accordance with claim 1 wherein ammonia is present during said contacting of said mixed isomeric methylene-bridged polyphenyl polyamine mixture with said nickel-containing hydrogenation catalyst, said ammonia being present in a molar ratio of between about 3:1 to about 30:1 moles ammonia per mole of mixed isomeric methylene-bridged polyphenyl polyamine mixture.

7. A process in accordance with claim 1 wherein said mixed isomeric methylene-bridged polyphenyl polyamine mixture is initially contacted, in the presence of said hydrogen, with said nickel-containing hydrogenation catalyst at a temperature of between about 150° to about 210°C. under a pressure of about 1,500 to about 3,500 psig.

8. A process in accordance with claim 1 wherein said contacting of said mixed isomeric methylene-bridged polyphenyl polyamine mixture with said nickel-containing hydrogenation catalyst is carried out in the presence of an organic liquid solvent.

9. A process in accordance with claim 1 wherein said mixed isomeric methylene-bridged polyphenyl polyamine mixture is then hydrogenated by heating said mixture with hydrogen in the presence of said ammonia and said ruthenium-containing hydrogenation catalyst at a temperature within the range of about 180° to about 210°C. under a pressure of between about 1,500 to about 3,500 psig.

10. A continuous process for preparing isomeric methylene-bridged polycyclohexylpolyamines in high yields from mixed isomeric methylene-bridged polyphenyl polyamine mixtures containing ruthenium-containing hydrogenation catalyst poisons, said continuous process comprising:
    injecting flowing streams of a mixed isomeric methylene-bridged polyphenyl polyamine mixture and hydrogen into a first zone having a temperature of from about 25°C to about 250°C, a pressure of between about 500 to about 15,000 psig and containing a nickel-containing hydrogenation catalyst, said flowing streams being injected at respective flow rates sufficient to form a flowing mixture stream having at least 100% molar excess hydrogen based upon said polyamine mixture;
    passing said flowing mixture stream through said first zone containing said nickel-containing hydrogenation catalyst to provide intimate contacting of said flowing mixture stream with said catalyst for a time effective in substantially inactivating said ruthenium-containing hydrogenation catalyst poisons;
    passing the effluent flowing from the first zone and ammonia through a second zone having a temperature of about 150° to about 250°C, a pressure of between about 500 to about 15,000 psig and containing a ruthenium-containing hydrogenation catalyst, said ammonia being passed at a rate sufficient to provide a molar ratio of about 3 to about 30 moles ammonia per mole of polyamine mixture; and recovering the isomeric methylene-bridged polycyclohexylpolyamines from the effluent flowing from said second zone.

11. The continuous process of claim 10 wherein said flowing stream of isomeric methylene-bridged polyphenyl polyamines mixture is comprised of isomeric methylenedianiline and higher functionality polyphenyl polyamines, said mixture having an average functionality of from about 2.0 to about 3.3.

12. The continuous process of claim 10 wherein said flowing stream of isomeric methylene-bridged polyphenyl polyamines mixture is comprised of at least 25% by weight isomeric methylenedianiline.

13. A process in accordance with claim 10 wherein said mixed isomeric methylene-bridged polyphenyl polyamine mixture has a functionality of between about 2.2 to about 2.7.

14. A continuous process in accordance with claim 10 wherein said first zone containing said nickel-containing hydrogenation catalyst has a temperature of between about 150°C. to about 210°C. and a pressure of between about 1,500 to about 3,500 psig and said second zone containing said ruthenium-containing hydrogenation catalyst has a temperature of between about 180°C. to about 210°C. and a pressure of between about 1,500 to about 3,500 psig.

15. The continuous process of claim 10 wherein said ammonia is injected as a flowing stream into said first zone at a flow rate sufficient to form said flowing mixture stream having a molar ratio of from about 3:1 to about 30:1 moles ammonia per mole mixed isomeric methylene-bridged polyphenyl polyamine mixture.

16. The continuous process of claim 15 wherein said flowing stream of isomeric methylene-bridged polyphenyl polyamines mixture is first admixed prior to said injection with an organic liquid solvent.

17. The continous process of claim 16 wherein said flowing streams of polyamine mixture and solvent, hydrogen and ammonia are passed through said first and second zones at a space velocity of between about 0.5 to about 2.0 g. total liquid feed per ml. catalyst per hour.

* * * * *